United States Patent
Meade

[11] Patent Number: 6,055,986
[45] Date of Patent: May 2, 2000

[54] APPARATUS AND METHOD FOR THE REDUCTION OF SNORING

[76] Inventor: Thomas E. Meade, 215 16th St. SW., Albuquerque, N. Mex. 87104

[21] Appl. No.: 08/850,705

[22] Filed: May 2, 1997

Related U.S. Application Data

[63] Continuation-in-part of application No. 08/633,163, Apr. 16, 1996, abandoned, which is a continuation-in-part of application No. 08/420,597, Apr. 12, 1995, Pat. No. 5,682,903, which is a continuation of application No. 08/354,139, Dec. 6, 1994, Pat. No. 5,467,783, which is a continuation of application No. 07/977,266, Nov. 16, 1992, abandoned.

[51] Int. Cl.⁷ ....................................................... A61F 5/56
[52] U.S. Cl. ........................... 128/848; 128/859; 602/902
[58] Field of Search .................................... 128/846, 848, 128/859–862; 2/2; 602/902

[56] References Cited

U.S. PATENT DOCUMENTS

| | | |
|---|---|---|
| 1,674,336 | 6/1928 | King . |
| 3,730,179 | 5/1973 | Williams . |
| 4,304,227 | 12/1981 | Samelson . |
| 4,715,368 | 12/1987 | George . |
| 4,901,737 | 2/1990 | Toone . |
| 5,003,994 | 4/1991 | Cook . |
| 5,092,346 | 3/1992 | Hays et al. . |
| 5,117,816 | 6/1992 | Shapiro ..................................... 128/861 |
| 5,277,202 | 1/1994 | Hays ......................................... 128/848 |
| 5,313,960 | 5/1994 | Tomasi . |
| 5,365,945 | 11/1994 | Halstrom .................................. 128/848 |
| 5,375,593 | 12/1994 | Press . |
| 5,409,017 | 4/1995 | Lowe ........................................ 128/848 |
| 5,427,117 | 6/1995 | Thornton . |
| 5,467,783 | 11/1995 | Meade . |
| 5,499,633 | 3/1996 | Fenton ...................................... 128/848 |
| 5,513,634 | 5/1996 | Jackson . |
| 5,537,994 | 7/1996 | Thornton . |
| 5,566,683 | 10/1996 | Thornton . |
| 5,570,704 | 11/1996 | Buzzard ................................... 128/848 |
| 5,678,567 | 10/1997 | Thornton et al. . |
| 5,718,244 | 2/1998 | Thornton . |
| 5,752,510 | 5/1998 | Goldstein . |
| 5,755,219 | 5/1998 | Thornton . |

FOREIGN PATENT DOCUMENTS

WO94/23673  10/1994  WIPO .

*Primary Examiner*—Michael A. Brown
*Attorney, Agent, or Firm*—Burns, Doane, Swecker & Mathis, L.L.P.

[57] ABSTRACT

An apparatus for intra-oral use including a framework having an upper curved platform and a lower curved platform, each of the platforms being defined by two walls extending from and separated by a floor, a material bonded to the upper and lower curved platform adapted to be molded in a shape suitable for relatively snugly receiving maxillary teeth of a user and for relatively loosely receiving mandibular teeth of the user when the user's mouth is closed in a normal closing arch, and a cavity formed between the upper and lower platforms adapted to receive the tongue of the user. The apparatus may also include an adjustment mechanism for adjusting a position of the upper platform with respect to the lower platform.

6 Claims, 11 Drawing Sheets

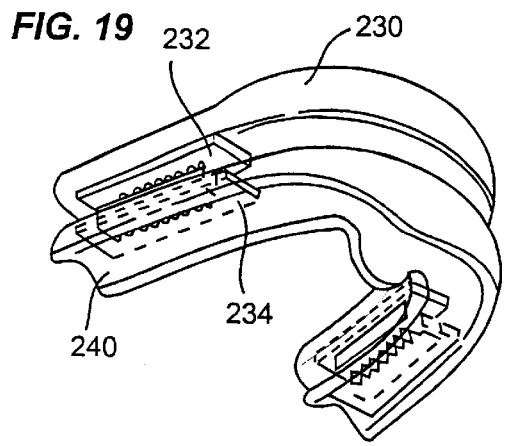
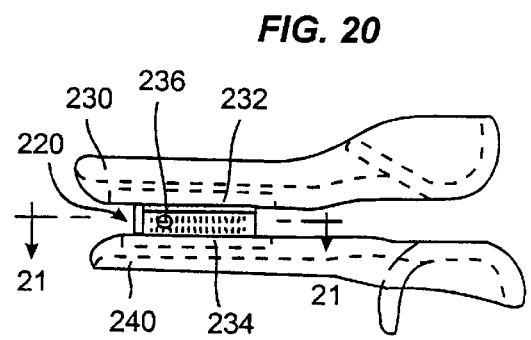
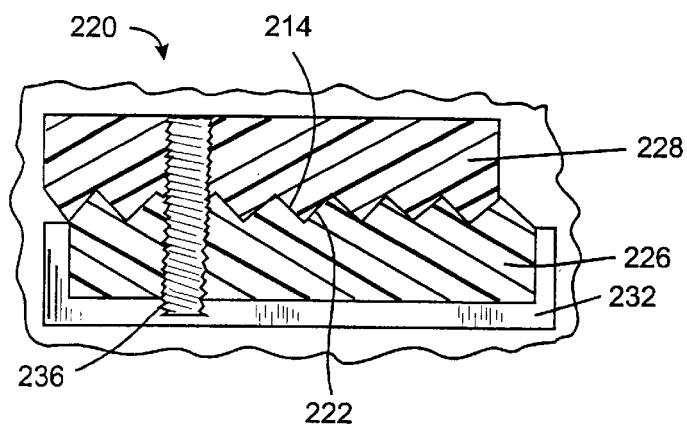
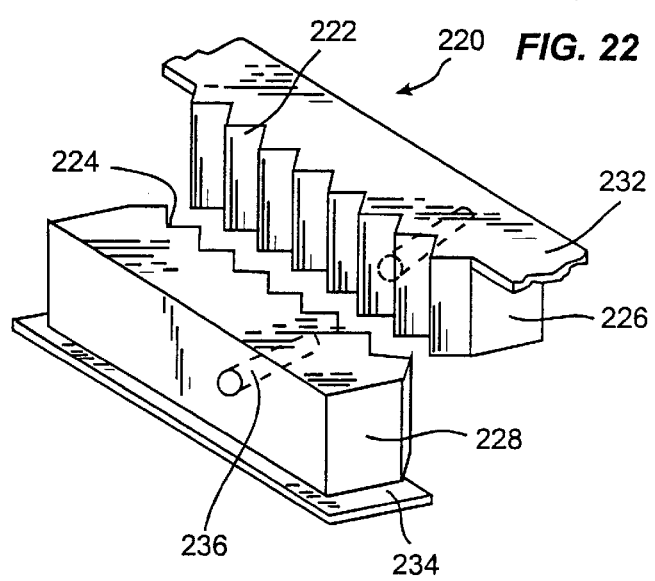

APPARATUS AND METHOD FOR THE REDUCTION OF SNORING

This is a continuation-in-part of application Ser. No. 08/633,163, filed Apr. 16, 1996, now abandoned, which is a continuation-in-part of application Ser. No. 08/420,597, filed Apr. 12, 1995, now U.S. Pat. No. 5,682,903, which is a continuation of Application Ser. No. 08/354,139, filed Dec. 6, 1994, now U.S. Pat. No. 5,467,783, which is a continuation of Application Ser. No. 07/977,266, filed Nov. 16, 1992, now abandoned.

BACKGROUND OF THE INVENTION

The present invention relates to an oral apparatus for use in the treatment of snoring, and particularly to a dental orthosis for use during sleep to treat snoring.

Lay people are commonly familiar with the symptoms of snoring, so little need be said in this regard. In mild cases, it may be a cause of amusement and only minor inconvenience. In more severe cases, however, it can disrupt sleep and even be a manifestation of a serious condition such as obstructive sleep apnea (OSA) syndrome, in which the sufferer must be awakened.

The major methods of treatment and aids to patients with obstructive problems of breathing were developed by Friedrick von Esmarch. As a military surgeon during the many wars in central Europe in the 19th century, he observed that many battlefield deaths occurred due to blood loss and/or strangulation. The principles that he developed to maintain an airway are still the primary principles in use today.

The simple, if somewhat crude, method that he used was to pull the tongue forward and to maintain this position by placing a skewer through the exposed part. This accomplished three major changes that form the principles which he recorded. The tongue was forward and largely clear of the throat, the jaws were open, and the lower jaw was moved forward. These three actions provided a considerable increase in the available airway of the oral pharynx.

Von Esmarch made another oral device which fitted to the teeth of the upper and lower jaw and by using his previously developed principles, this device produced a more open airway without pain or injury to the tongue.

Almost all devices developed and used for this purpose during the twentieth century employ the same basic form and functions of the von Esmarch device. The advent of modern dentistry has permitted refinement and improvements which enhance the aid to the patient with increased tolerance and comfort. There have been many patents issued for devices to help control snoring and obstructive sleep apnea. Most of them follow the von Esmarch principles.

For example, U.S. Pat. No. 1,674,336 to King discloses a respirator which includes upper and lower channels to support the upper and lower teeth respectively. The device is provided with a central air passage which opens into channels through which air is exhaled. Projections are provided integral with an upper portion of the body of the device, defining between them an air channel. These projections support the tongue so that it does not block the air passages. In practice, this device is ineffective since the position of the tongue is such that the air passages are blocked.

At least one device provides a tongue chamber in front of the mouth. By creating a vacuum in this chamber, the tongue is held forward into the chamber. The device is held in place by fixation to the teeth of the upper jaw. A similar type of device, disclosed in U.S. Pat. No. 4,304,227 to Samelson, includes channels for insertion of the upper and lower teeth and a socket into which the tongue is inserted. The tongue is held in place in the socket. The Samelson device prevents air from escaping from the patient's mouth by a front plate which, when inserted, fits over the exterior portion of the patient's lips. The jaws are locked together during use and the tongue is prevented from resting in its normal position. This type of device may cause problems if the patient's nasal passages are clogged or if the patient coughs or vomits during sleep.

U.S. Pat. No. 4,715,368 to George discloses a device which includes upper and lower channels, including depressions into which the teeth fit. A beak with an orifice at the front end is provided in the center of the mouthpiece which parts the lips to allow air to pass through. The tongue is held in place by flanges extending inwardly from the lower channel. This device has attendant disadvantages in that it locks the jaws together and advances the lower jaw forward causing mandibular repositioning. This causes aggravation of tempo mandibular joint problems and wearer discomfort.

Another type of device is disclosed in U.S. Pat. No. 4,901,737 to Toone. This device is a form of the von Esmarch device but with a marked exaggeration of opening of the jaw wedge. This type of device, which is completely open in the front and preferably open at the top, across the palatal arch, requires mouth breathing, and so causes many complications, such as excess salivation and/or dry mouth. Such a device would be contraindicated in moderately severe or severe OSA. This device locks the jaws together and also repositions the mandible in an open and protrusive position, as compared with the normal closed position of the jaw. This displacement can cause discomfort and aggravate problems with the tempo mandibular joint.

U.S. Pat. No. 5,003,994, issued to Cook, discloses an oral apparatus for reducing snoring and preventing sleep apnea which has a rigid shell with an upper tray, a lower cam structure to advance the mandible structure (lower jaw) forward with respect to the maxilla structure (upper jaw), stops to hold the mouth partially open, and a soft resilient pliable socket inside of the tray. This device is fitted such that the mandible is advanced forward with respect to the maxilla. Thus, this device suffers from the same drawbacks as the Toone device regarding discomfort and potential tempo mandibular joint problems.

U.S. Pat. No. 5,092,346 to Hays et al., provides a dental device which provides a channel for receiving the upper teeth and a ramp formed on the bottom portion to cam the lower jaw forward. The ramp surface engages the lower anterior teeth in a manner such that the lower jaw is moved into a more forward position than normal. This device, by displacing the lower jaw in a more forward position, also causes problems with the tempo mandibular joint and pain and discomfort during use.

Both the Cook and the Hays et al. patents include breathing apertures between the upper and lower channels. These apertures are closed by the natural movement of the tongue during use, thus causing breathing problems.

U.S. Pat. No. 5,117,816 to Shapiro et al. provides an anti-snoring device which includes an upper surface portion which substantially covers all the upper teeth and a lower surface portion which contacts substantially all the lower teeth. An airway passage is provided in the center of the mouthpiece to permit breathing. The device includes a downwardly extending flange intended to extend into the lingual (tongue side of the teeth) vestibule of the user to maintain a forward posture of the lower jaw. This device also may cause pain and discomfort during use due to the forward placement of the jaw.

Though not designed as anti-snoring devices, mouthguards, such as those sometimes used by athletes, provide upper and lower channels into which the teeth are inserted. The pliant material used to form the mouthguards are fitted to the individual by insertion into the person's mouth, after having been heated to soften the material. These devices are not suitable for use as anti-snoring devices since they provide no means by which the tongue is held in a forward position so as to prevent blockage of the esophageal airway. There is no space provided at all sufficient to receive the tongue between the upper and lower channels. Additionally, these devices serve to lock the jaws together and prevent natural movement.

The KLEARAWAY Oral Appliance developed by Dr. Alan Lowe is a device for the treatment of snoring and OSA. However, this device has disadvantages in that it locks the jaws together and advances the lower jaw forward causing mandibular repositioning. This may cause aggravation of tempo mandibular joint problems and wearer discomfort.

In addition to the above mentioned deficiencies, prior devices have also failed to accurately position the maxillary and mandibular teeth in the proper relative positions. Typically, in constructing an oral apparatus, the doctor would have the patient protrude the mandible at the doctor's instructions, which was often not easily controlled, resulting in a misaligned apparatus. If the protrusion was not correct, it would then be necessary to either refit the apparatus to provide the proper positioning or to fabricate a completely new device.

SUMMARY OF THE INVENTION

It is an object of the present invention to provide a method and apparatus for reducing snoring that overcomes the above described disadvantages.

According to one embodiment of the invention, an apparatus for intra-oral use comprises upper means for snugly fitting over maxillary teeth of a user, lower means, connected to the upper means, for loosely fitting over mandibular teeth of the user so as to allow the mandibular teeth to approach the maxillary teeth and come to rest in a normal closing arch such that a relative position of the maxillary teeth and the mandibular teeth when the apparatus is worn is the same as when the apparatus is not worn and to allow freedom of movement of the mandible in forward and side to side directions while preventing rear movement of the mandible, and adjustment means, connected to the upper and lower means, for adjusting a position of the upper means with respect to a position of the lower means.

According to one embodiment of the invention, an oral apparatus is provided which comprises upper means for receiving maxillary teeth of a user, lower means, connected to the upper means, for receiving mandibular teeth of a user so as to allow the mandibular teeth to approach the maxillary teeth and come to rest in a normal closing arch such that a relative position of the maxillary teeth and the mandibular teeth when the apparatus is worn is the same as when the apparatus is not worn, and adjustment means connected to the upper and lower means for adjusting a position of the upper means with respect to a position of the lower means.

According to one embodiment of the invention, an oral apparatus is provided which comprises upper means for receiving maxillary teeth of a user, lower means, connected to the upper means, for receiving mandibular teeth of a user and for allowing freedom of movement of the mandible in forward and side to side directions while preventing rear movement of the mandible, and adjustment means, connected to the upper and lower means, for adjusting a position of the upper means with respect to a position of the lower means.

Still other objects, features and attendant advantages of the present invention will become apparent to those skilled in the art from a reading of the following detailed description of the embodiments constructed in accordance therewith, taken in conjunction with the accompanying drawings.

BRIEF DESCRIPTION OF THE DRAWINGS

The invention of the present application will now be described in more detail with reference to the preferred embodiments of the device, given only by way of example, and with reference to the accompanying drawings, in which:

FIG. 19 is a perspective view of another embodiment of the invention which comprises upper and lower members;

FIG. 20 is a side view of the apparatus shown in FIG. 19;

FIG. 21 is a cross-sectional view of the apparatus shown in FIG. 20;

FIG. 22 is an expanded perspective view of the adjustment mechanism shown in FIG. 19;

GENERAL DESCRIPTION OF THE PREFERRED EMBODIMENTS

Figure 1:
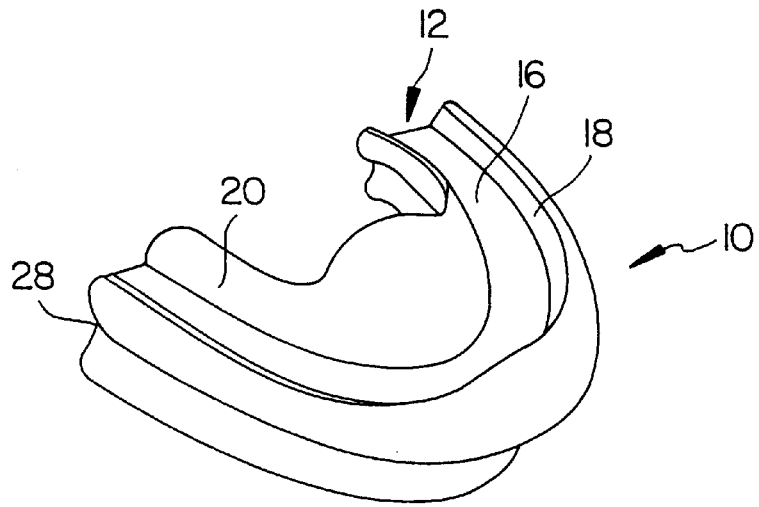
FIG. 1 is a perspective view of the shell of the apparatus according to the present invention.

The present invention relates to an oral apparatus for use in the treatment of snoring, and particularly to a dental orthosis for use during sleep to eliminate or substantially reduce loud snoring. The anti-snoring device according to the present invention consists of a substantially semi-circular hard shell or framework that holds a soft, moldable thermoplastic material. The molded material forms snugly over the maxillary (upper) teeth, thus preventing the appliance from being dislodged. The mandibular (lower) teeth will fit loosely into the moldable material in such a way that the lower jaw can open, close and move from side to side.

The hard framework with a thin layer of moldable material extends posteriorly over the bicuspids and molars in such a way as to prevent supra eruption of these teeth. The anti-snoring device according to the present invention is designed and fitted to allow the mouth to close in the normal arch of closure and not to forcefully thrust the mandible forward to prevent trauma to the tempo mandibular joint and eliminate discomfort during use. This new device also allows complete freedom of movement of the mandible side to side, but does not allow the mandible to drop backwards. The device also allows voluntary, natural movement of the lower jaw forward while not forcing such forward movement.

The hard shell of the appliance has an area between the anterior maxillary and mandibular teeth into which the tongue protrudes during use. Thus, by opening the jaws slightly, enough for the tongue to move forward into the global cavity provided for it, the base of the tongue will be rotated downward and forward, opening the airway. This opening of the airway is further enhanced by the natural reflex of the tongue to slide forward into the cavern between the front teeth, with the resulting elimination or substantial reduction of snoring.

This appliance is safer than previous oral anti-snoring appliances, since the two jaws are not "locked" together, allowing the wearer to sneeze, cough, or even vomit, around the appliance and not aspirate. The channel which is provided along the outer side of the appliance in a preferred embodiment of the appliance facilitates oral breathing if the nasal passages are closed. However, with a normal patent opened nasal airway, the appliance discourages oral breathing and permits proper nasal breathing.

According to another embodiment, the present invention comprises a pair of upper and lower substantially semi-circular hard shells or members that hold a soft, moldable thermoplastic material. In the upper member, the molded material forms snugly over the maxillary (upper) teeth, thus preventing the appliance from being dislodged. In the lower member, the mandibular (lower) teeth will fit loosely into the moldable material in such a way that the lower jaw can open, close and move from side to side. The upper and lower members may be held in a fixed relationship to each other by an adjustment device.

The adjustment device is fixed to the upper and lower members and allows the relative positions of the upper and lower members to be adjusted in at least one dimension. The adjustment device may thus include longitudinal screws which control forward and rearward adjustment of the upper member relative to the lower member, and/or vertical screws which control a separation distance between a bottom surface of the upper member and a top surface of the lower member. The adjustment device may also include a periodic interlocking surface formed as part of the upper member which interlocks with a reciprocal discrete or periodic interlocking surface formed as part of the lower member.

The upper and lower members with a thin layer of moldable material extend posteriorly over the bicuspids and molars in such a way as to prevent supra eruption of these teeth. The anti-snoring device according to this embodiment of the present invention is designed and fitted to allow the mouth to close in the normal arch of closure and not to forcefully thrust the mandible forward to prevent trauma to the tempo mandibular joint and eliminate discomfort during use. The device also allows complete freedom of movement of the mandible side to side, but does not allow the mandible to drop backwards. The device also allows voluntary, natural movement of the lower jaw forward while not forcing such forward movement.

The upper and lower members of the appliance define an area between the anterior maxillary and mandibular teeth into which the tongue protrudes during use. Thus, by opening the jaws slightly, enough for the tongue to move forward into the global cavity provided for it, the base of the tongue will be rotated downward and forward, opening the airway. This opening of the airway is further enhanced by the natural reflex of the tongue to slide forward into the cavern between the front teeth, with the resulting elimination or substantial reduction of snoring.

This embodiment of the appliance is safer than previous oral anti-snoring appliances, since the two jaws are not "locked" together, allowing the wearer to sneeze, cough, or even vomit, around the appliance and not aspirate. The channel which is provided along the outer side of the appliance in a preferred embodiment of the appliance facilitates oral breathing if the nasal passages are closed. However, with a normal patent opened nasal airway, the appliance discourages oral breathing and permits proper nasal breathing.

DETAILED DESCRIPTION OF THE PREFERRED EMBODIMENTS

FIG. 1 is a perspective view of the shell 10 of the apparatus according to a preferred embodiment of the present invention. The semi-circular shell 10 is made of a rigid or semi-rigid material which may be injection molded to create the desired shape. A single piece of plastic may be used to form the shell. One such material is methylmethacrylate, which is a plastic material used for dentures. After the device is fitted, it may be cured. The curing process prevents undesirable absorption of mouth fluids, or cleaning fluids, and presents a smooth non-irritating surface to the soft tissues of the mouth.

Alternatively, according to a preferred embodiment, this device may be made from a resilient semi-rigid polycarbonate resin thermoplastic. The resin preferably has a specific gravity of about 1.20, a tensile strength (yield) of about 9000 and a softening temperature of about 310° F. One such material is sold by General Electric Company under the name of Lexan™, though other comparable materials may be used.

For purposes of ease of description, the terms upper, lower, front and rear have been used. It is understood that these relative terms describe the device in its normal in-use position. That is, upper and lower refers to the portions of the apparatus which receive the maxillary and mandibular teeth respectively, front refers to that portion of the device facing the outside of the mouth and rear refers to that portion facing the rear of the mouth toward the throat.

Figure 2:
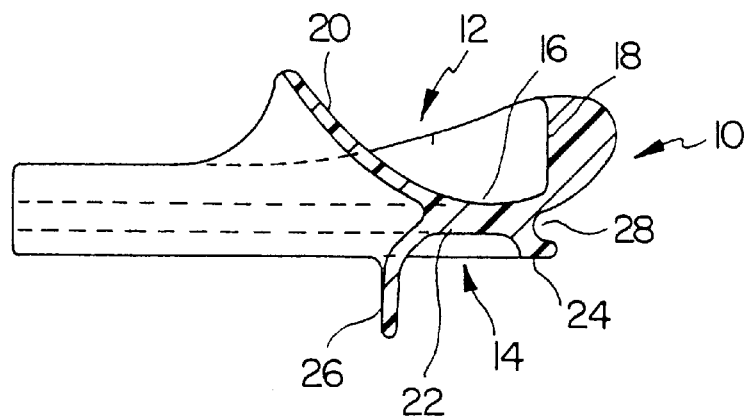
FIG. 2 is a cross-sectional view of the shell of the apparatus according to the present invention.

Referring to FIGS. 1 and 2, the shell 10 is provided with upper and lower platforms 12 and 14, respectively. The upper platform 12 is defined by front and rear walls or flanges 18 and 20, respectively, extending upwardly from the platform floor 16. The lower platform 14 is defined by front and rear walls or flanges 24 and 26, respectively, extending downwardly from the platform floor 22. The rear flange 26 extends substantially perpendicular with respect to the floor 22 of the lower platform 14. At the intersection of the front sides of the upper front wall 18 and the lower front wall 24, an outer channel 28 is formed around the outer circumference of the apparatus. The front side of the shell 10 is solid, and impervious to air. In particular, there is no aperture to permit breathing through the device when the device is positioned in the mouth. If the wearer wishes to breathe through the mouth at all, it is necessary to draw air around the periphery of the device as described below.

Figure 3:
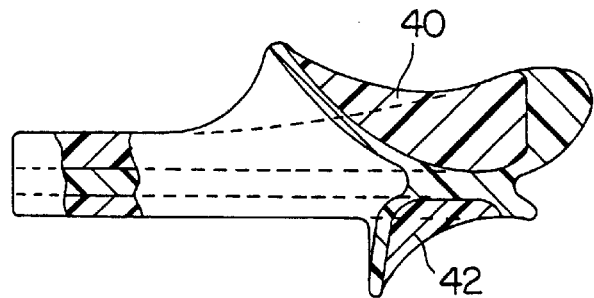
FIG. 3 is a cross-sectional view of the shell of the apparatus fitted with a moldable material according to the present invention.

Resin layers 40, 42, respectively, are bonded to the platforms 12 and 14 (FIG. 3). These layers may be formed from an ethylene-vinyl acetate copolymer resin, and preferably from a resin having a softening and molding temperature of about 150° F. One such material is sold by the Du Pont Company under the name of Elvax™.

According to a preferred embodiment of the present invention, the resin layers are formed from material which can be easily molded in the user's mouth and thus conform to the configuration of the user's upper teeth and normal closing arch. This results in significant cost savings due to a reduction in the time required for fabrication, fitting, and adjustment of the device. Further, the fitting of the device to allow for retention of the normal closing arch of the user provides a significant advantage over other known devices. This advantage results from the elimination of the potential problems with the tempo mandibular joint and the substantial increase in comfort for the user during use.

Individual fitting of the apparatus to fit the user's normal closing arch and teeth is simplified by the formation of the apparatus from a shell of a polycarbonate resin thermoplastic and having layers of acetate copolymer resin bonded thereto. According to a preferred embodiment, the acetate copolymer resin layer is about 3 to 4 millimeters in thickness in the platform. Preferably, the acetate copolymer resin has a substantially lower softening and molding temperature than that of the polycarbonate resin-thermoplastic forming the shell. This simplifies the individual fitting of the device to the user's mouth.

To fit the device to a particular user, the device is immersed in a hot fluid, preferably water, to impart a yielding nature to the acetate copolymer resin layer. In this manner, the resin layer accepts the user's distinctive tooth and dental closing arch configuration during the fitting process.

Once the acetate copolymer resin is sufficiently moldable, the device is forcibly inserted against the user's upper jaw and teeth. The user then closes his/her mouth in a normal manner. This causes the lower teeth to be pressed against the resin layer in the lower platform. Upon cooling to ambient temperature, the acetate copolymer resin retains the user's tooth configuration, for ease of repeat placement by the user. Excess resin can be cut from the device to make the device more comfortable in use.

It is important for the proper fitting of this device that the user is instructed to close his/her mouth normally, so that the fitted apparatus does not cause any unnatural forward movement of the lower jaw. In other words, when the apparatus according to the present invention is fitted in the user's mouth, the lower jaw is in substantially the same position as it is when the device is not inserted in the mouth, so that with respect to the upper jaw the normal closing arch of the user is maintained. When the fitted apparatus is inserted in the user's mouth, the device allows complete freedom of natural movement of the lower jaw side to side, but does not allow the lower jaw to drop backwards. However, as noted above, while forward movement of the lower jaw is permitted, the lower jaw is not forced into an unnatural forward placement during use.

When fitted properly, the maxillary teeth are firmly engaged in the moldable material on the upper platform 12. The maxillary teeth back to approximately the first molars on each side have the occluding surfaces indented in the moldable material. The lower teeth go into the area provided by the lower platform 14. This area should only be a rest or a stop for these teeth, so that the jaw will not be allowed to close all the way to its normal point of closure. The fitted apparatus allows the jaw to move and barely has the teeth indented in it. The lower platform 14 extends back to about the first molars and possibly to the second molar, to prevent super eruption of the teeth, to allow the jaws to be supported, and to prevent pain.

Figure 4:
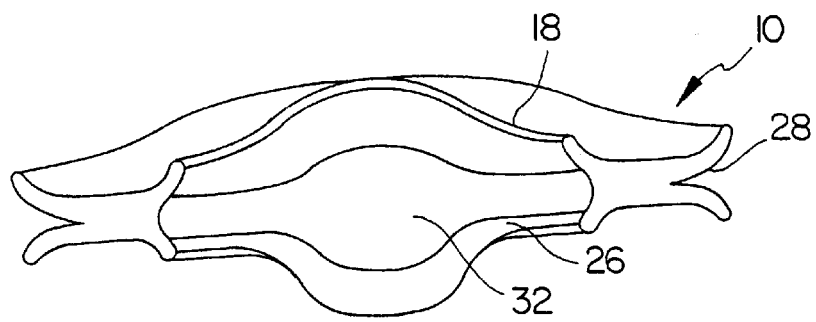
FIG. 4 is a rear view of the shell of the apparatus according to the present invention.

FIG. 4 illustrates a rear view of the shell 10 apparatus. As described above, a channel 28 is formed on the front side of the apparatus at the intersection of the upper front wall 18 and the lower front wall 24. The channel 28 forms an air passage around the outside of the apparatus when it is inserted during use. In the inside surface of the apparatus, a cavity 32 is formed at the intersection of the rear side of the upper rear wall 20 and the lower rear wall 26. The tongue rests in the cavity 32 by natural reflexive movement when the apparatus is in use to open the esophagal airway.

Figure 5:
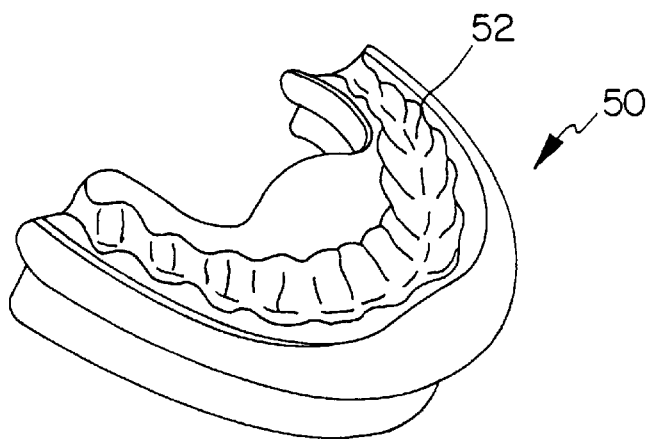
FIG. 5 is a perspective view of a fitted apparatus according to the present invention.

FIG. 5 illustrates an apparatus 50 which has been fitted to a user's mouth. Teeth impressions 52 are formed when the apparatus is inserted against the upper jaw and teeth as described above. The lower teeth also form impressions, which are not shown in the drawings.

Figure 6:
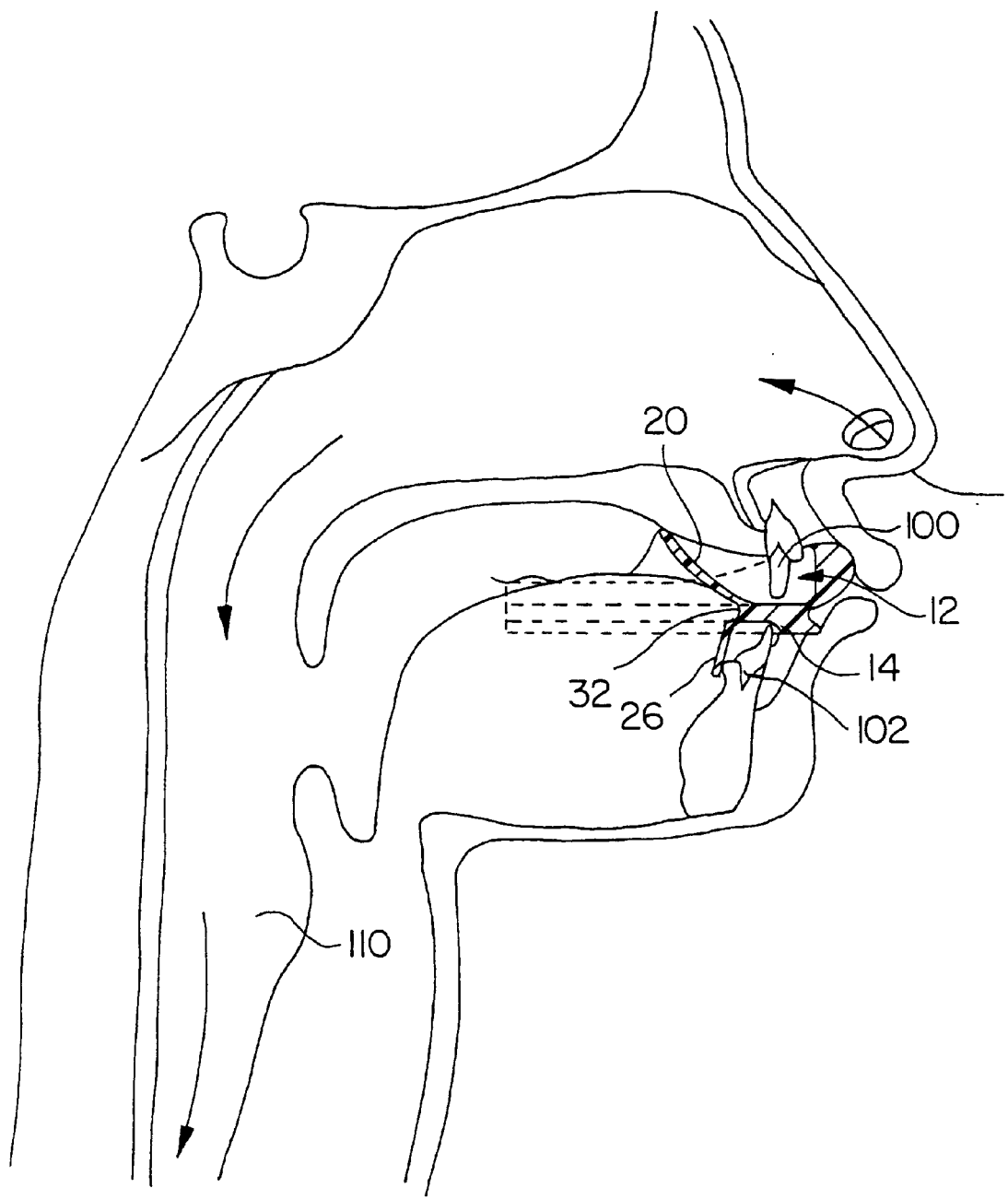
FIG. 6 is a cutaway view of the air passages of a person fitted with the apparatus according to the present invention.

FIG. 6 illustrates an apparatus in its in-use position in the mouth. For purposes of clarity, the resin layer has been omitted. The upper teeth 100 are snugly inserted in the impressions (not shown) in the upper platform 12. The lower teeth 102 rest in the impressions (not shown) in the lower platform 14 and are prohibited from backward movement by the wall or flange 26 of the lower platform 14. When the apparatus is inserted, the mandibular teeth approach the maxillary teeth and come to rest in a normal closing arch, with the jaws separated from each other by the apparatus.

The user's tongue (not shown) slides into the cavity 32 formed by the rear portion of the wall 20 forming the upper platform 12 and the wall 26 forming the lower platform 14. Specifically, by opening the jaws slightly, an amount sufficient for the tongue to move forward into the cavity 32 provided for it, the base of the tongue is rotated downward and forward into the cavity 32 between the teeth, with the resulting opening of the esophageal air passageway 110.

The apparatus is constructed to fit loosely in the mouth so that the jaws are not locked together. In this manner the user can sneeze, cough or even vomit around the apparatus and not aspirate. The channel 28 formed around the outside of the apparatus by the upper and lower outer walls 18 and 24, respectively, facilitates oral breathing if the nasal passages are closed. However, with a normal patent nasal airway, as shown by the arrows on FIG. 6, the apparatus will discourage oral breathing and permit proper nasal breathing.

Exemplary embodiments of the invention which allow adjustment of the position of the upper platform with respect to the lower platform will now be described.

Figure 7:
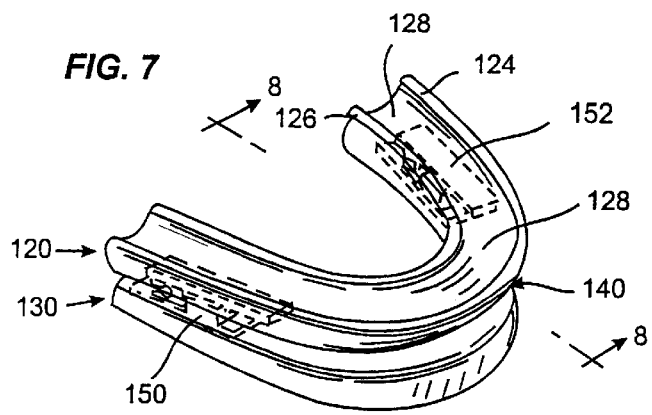
FIG. 7 is a perspective view of one embodiment of the invention which comprises upper and lower members.

FIG. 7 is a perspective view of upper and lower members 120 and 130 of the apparatus according to a preferred embodiment of the present invention. The upper and lower members 120 and 130 are made of a rigid or semi-rigid material which may be injection molded to create the desired shape. A single piece of plastic may be used to form each member. One such material is methylmethacrylate, which is a plastic material used for dentures. After the device is fitted, it may be cured. The curing process prevents undesirable absorption of mouth fluids, or cleaning fluids, and presents a smooth non-irritating surface to the soft tissues of the mouth.

Alternatively, according to a preferred embodiment, this device may be made from a resilient semi-rigid polycarbonate resin thermoplastic such as Lexan™, as described above. The resin preferably has a specific gravity of about 1.20, a tensile strength (yield) of about 9000 and a softening temperature of about 310° F.

Referring to FIGS. 7–10, the upper member 120 forms an upper platform and the lower member 130 forms a lower platform. The upper platform is defined by front and rear walls or flanges 124 and 126, respectively, extending upwardly from the upper platform floor 128. The lower platform is defined by front and rear walls or flanges 134 and 136 respectively, extending downwardly from the lower platform floor 138. The rear flange 136 preferably extends substantially perpendicularly with respect to the floor 138 of the lower platform. At the intersection of the outer sides of the upper front wall 124 and the lower front wall 134, an outer channel 140 is formed around the outer circumference of the apparatus. The user may breathe through the mouth by drawing air around the periphery of the device. The user may also breathe through the opening between the upper and lower members 120 and 130, if necessary.

Figure 8:
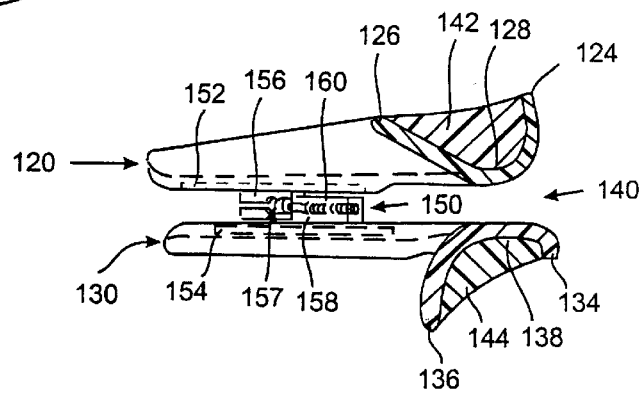
FIG. 8 is a cross-sectional view of the apparatus shown in FIG. 7.
Figure 9:
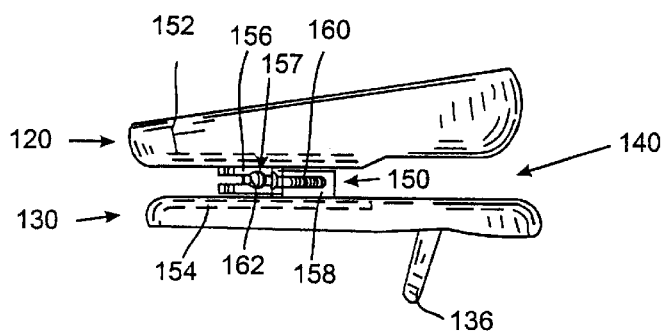
FIG. 9 is a side view of the apparatus shown in FIG. 7.

Resin layers 142 and 144 respectively, are bonded to the upper and lower platforms, as shown in FIG. 8. These layers may be formed from an ethylene-vinyl acetate copolymer resin, and preferably from a resin having a softening and molding temperature of about 150° F. One such material is sold by the Du Pont Company under the name of Elvax™.

According to a preferred embodiment of the invention, the resin layers 142 and 144 are formed from material which can be easily molded in the user's mouth and thus can conform to the configuration of the user's upper teeth and normal closing arch. This results in significant cost savings due to a reduction in the time required for fabrication, fitting, and adjustment of the device. Further, the fitting of the device to allow for retention of the normal closing arch of the user provides a significant advantage over other known devices. This advantage results from the elimination of the potential problems with the tempo mandibular joint and the substantial increase in comfort for the user during use.

Individual fitting of the apparatus to fit the user's normal closing arch and teeth is simplified by the formation of the apparatus from upper and lower members of a polycarbonate resin thermoplastic and having layers of acetate copolymer resin bonded thereto. According to a preferred embodiment, the acetate copolymer resin layer is about 3 to 4 millimeters in thickness in the upper and lower platforms. Preferably, the acetate copolymer resin has a substantially lower softening and molding temperature than that of the polycarbonate resin-thermoplastic forming the upper and lower members. This simplifies the individual fitting of the device to the user's mouth.

To fit the device to a particular user, the device is immersed in a hot fluid, preferably water, to impart a yielding nature to the acetate copolymer resin layer. In this manner, the resin layer accepts the user's distinctive tooth and dental closing arch configuration during the fitting process.

Once the acetate copolymer resin is sufficiently moldable, the device is forcibly inserted against the user's upper jaw and teeth. The user then closes his/her mouth in a normal manner. This causes the lower teeth to be pressed against the resin layer in the lower platform. Upon cooling to ambient temperature, the acetate copolymer resin retains the user's tooth configuration, for ease of repeat placement by the user. Excess resin can be cut from the device to make the device more comfortable in use.

The above described method of custom forming the device to the user's mouth is easily implemented due to the moldability of the acetate copolymer resin after being immersed in hot water. It will be readily apparent to those skilled in the art, however, that other methods of custom forming the device to the user's mouth can be implemented with the present invention. For example, the upper and lower members can be formed in a conventional manner from an impression taken of the user's maxillary and mandibular teeth. The impression is used to mold the upper and lower members, which are thereby custom fit to the user's mouth without the need for an acetate copolymer resin layer. This and other such variations in the method of custom forming the device are intended to fall within the scope of the present invention.

For the proper fitting of this device, the user is instructed to close his/her mouth normally, so that the fitted apparatus does not cause any unnatural forward movement of the lower jaw. In other words, when the apparatus according to the present invention is fitted in the user's mouth, the lower jaw is in substantially the same position as it is when the device is not inserted in the mouth, so that with respect to the upper jaw the normal closing arch of the user is maintained. When the fitted apparatus is inserted in the user's mouth, the device allows complete freedom of natural movement of the lower jaw side to side, but does not allow the lower jaw to drop backwards. However, as noted above, while forward movement of the lower jaw is permitted, the lower jaw is not forced into an unnatural forward placement during use. The apparatus according to the embodiment shown in FIGS. 7–10 also allows adjustment of the position of the upper member 120 with respect to the lower member 130 at any time during treatment, as will be described in more detail below.

When fitted properly, the maxillary teeth are firmly engaged in the moldable material on the upper platform formed by the upper member 120. The maxillary teeth back to approximately the first molars on each side have the occluding surfaces indented in the moldable material. The lower teeth go into the area provided by the lower platform of the lower member 130. This area should only be a rest or a stop for these teeth, so that the jaw will not be allowed to close all the way to its normal point of closure. The fitted apparatus allows the jaw to move and barely has the teeth indented in it. The lower platform extends back to about the first molars to prevent super eruption of the teeth, to allow the jaws to be supported, and to prevent pain.

Figure 10:
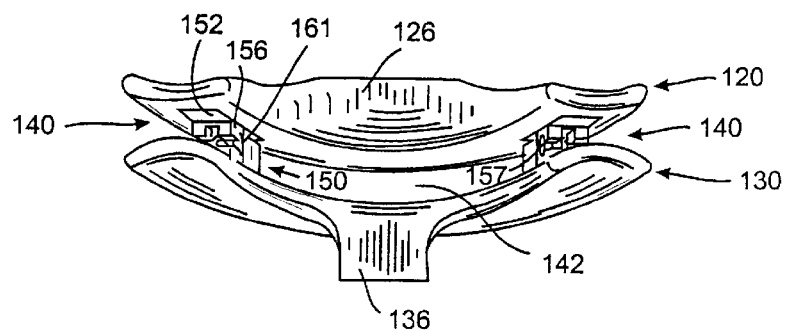
FIG. 10 is a rear perspective view of the apparatus shown in FIG. 7.

FIG. 10 illustrates a rear view of the apparatus. As described above, a channel 140 is formed on the front side of the apparatus adjacent to the outside surfaces of the upper front wall 124 and the lower front wall 134. The channel 140 forms an air passage around the outside of the apparatus when it is inserted during use. In the inside surface of the apparatus, a cavity 142 is formed between the upper and lower members 120 and 130 at the intersection of the rear side of the upper rear wall 126 and the lower rear wall 136. The tongue rests in the cavity 142 by natural reflexive movement when the apparatus is in use to open the esophagal airway.

When the apparatus has been fitted to a user's mouth, teeth impressions (not shown) are formed when the apparatus is inserted against the upper jaw and teeth, as described above with respect to FIG. 5. The lower teeth also form impressions.

Figure 11:
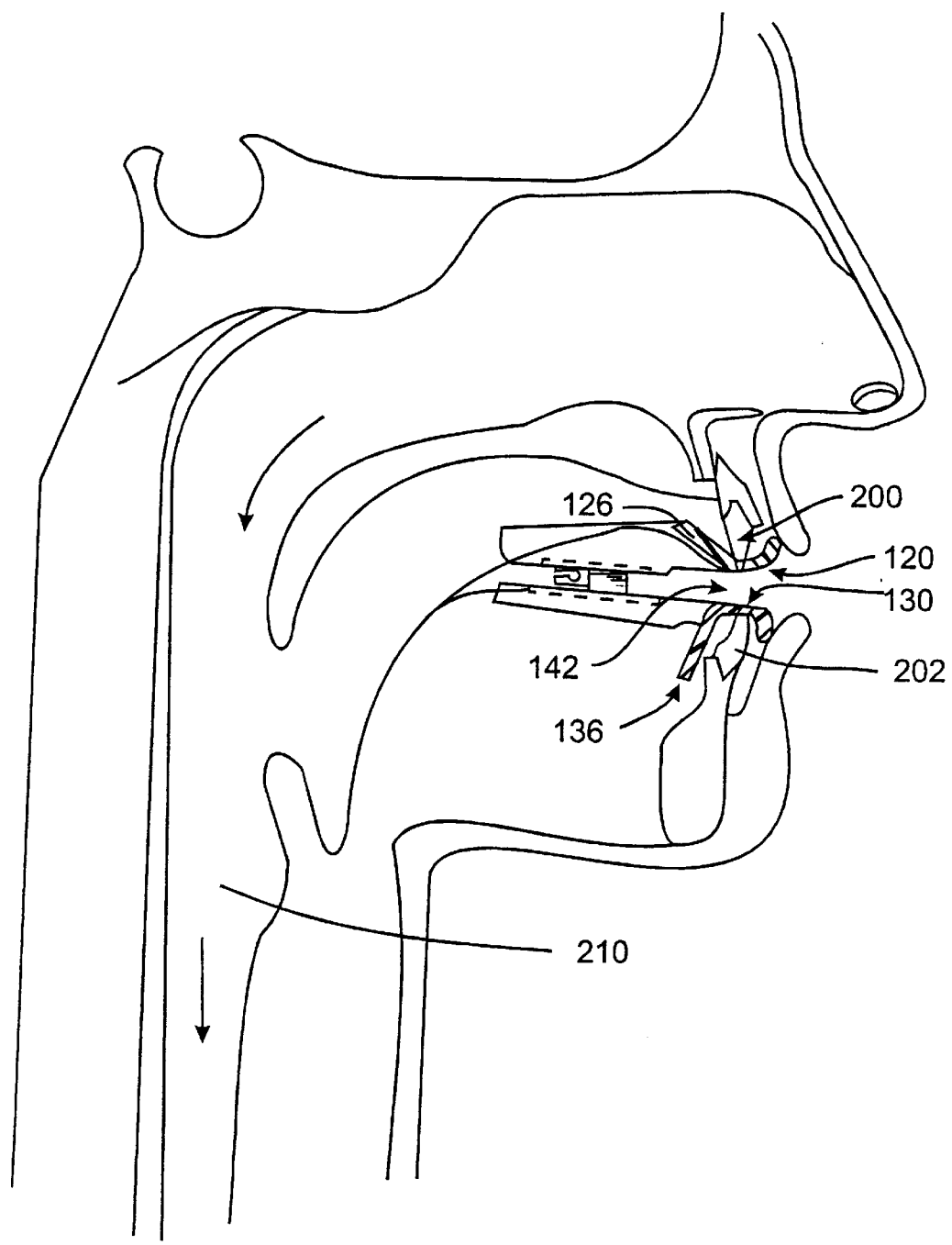
FIG. 11 is a cutaway view of the air passages of a person fitted with the apparatus of FIG. 7.

FIG. 11 illustrates an apparatus in its in-use position in the mouth. For purposes of clarity, the resin layer has been omitted. The upper teeth 200 are snugly inserted in the impressions (not shown) in the upper platform formed by the upper member 120. The lower teeth 202 rest in the impressions (not shown) in the lower platform formed by the lower member 130 and are prohibited from backward movement by the rear wall or flange 136 of the lower platform. When the apparatus is inserted, the mandibular teeth approach the maxillary teeth and come to rest in a normal closing arch, with the jaws separated from each other by the apparatus. The user's tongue (not shown) slides into the cavity 142 formed by the rear wall 126 of the upper platform and the rear wall 136 of the lower platform. Specifically, by opening the jaws slightly, an amount sufficient for the tongue to move forward into the cavity 142 provided for it, the base of the tongue is rotated downward and forward into the cavity 142 between the teeth, with the resulting opening of the esophageal air passageway 210.

The apparatus is constructed to fit loosely in the mouth so that the jaws are not locked together. In this manner the user can sneeze, cough or even vomit around the apparatus and not aspirate. The channel 140 formed around the outside of the apparatus by the upper and lower outer walls 124 and 134, respectively, facilitates oral breathing if the nasal passages are closed. However, with a normal patent nasal airway, as shown by the arrows in FIG. 11, the apparatus will discourage oral breathing and permit proper nasal breathing.

FIGS. 7–10 and 17–18 show an embodiment of the invention in which the upper and lower members 120 and 130 are connected together with an adjustment device 150. The adjustment device 150 fixes the upper and lower members 120 and 130 together on both the left and the right side of the upper and lower members. On each side (left and right) of the apparatus, the adjustment device 150 preferably comprises an upper plate 152 and a lower plate 154. The plates are embedded in the resilient semi-rigid material of the upper and lower members 120 and 130 at the rear molar area of the members. Projecting from the upper and lower plates on each side of the apparatus are blocks 156 and 158, respectively, which receive a longitudinal screw 160 for controlling the forward and backward movement of the upper member 120 with respect to the lower member 130. The adjustment device 150 can be formed of a metal such as stainless steel or any other suitable material such as a sufficiently strong plastic material.

Figure 18:
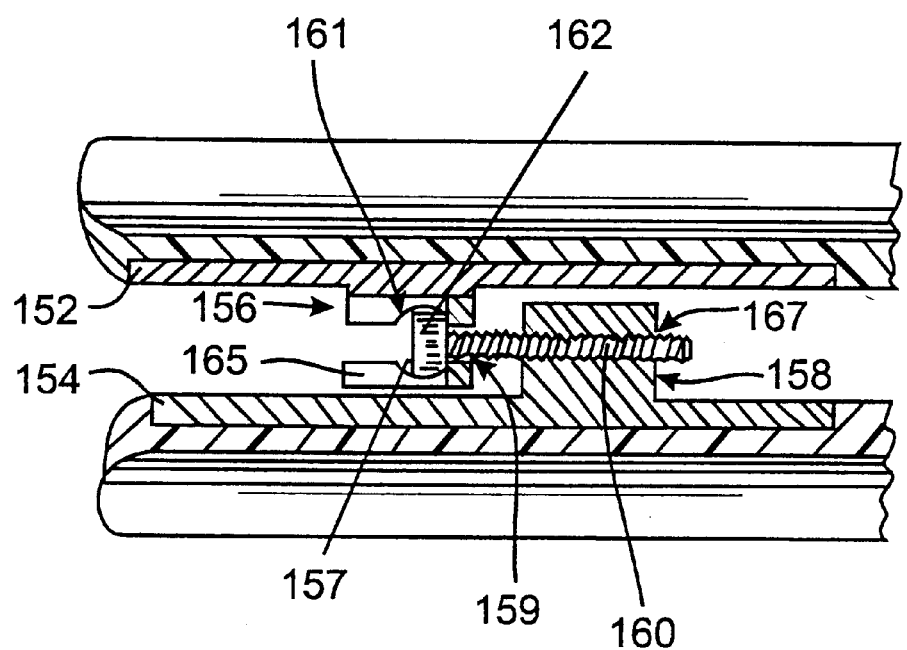
FIG. 18 is a side cross-sectional view of the exemplary adjustment mechanism shown in FIG. 7.
Figure 23:
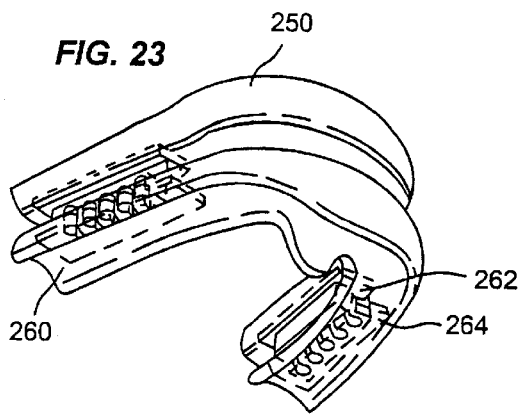
FIG. 23 is a perspective view of another embodiment of the invention which comprises upper and lower members.
Figure 24:
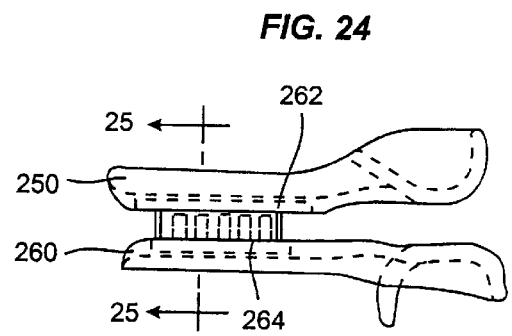
FIG. 24 is a side view of the apparatus shown in FIG. 23.
Figure 25:
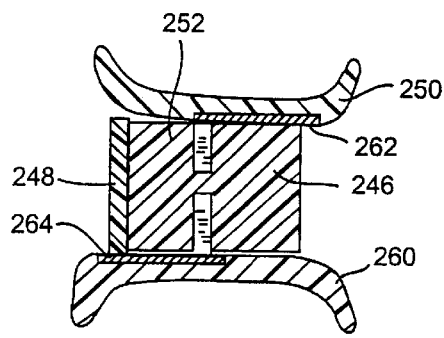
FIG. 25 is a cross-sectional view of the apparatus shown in FIG. 24.
Figure 26:
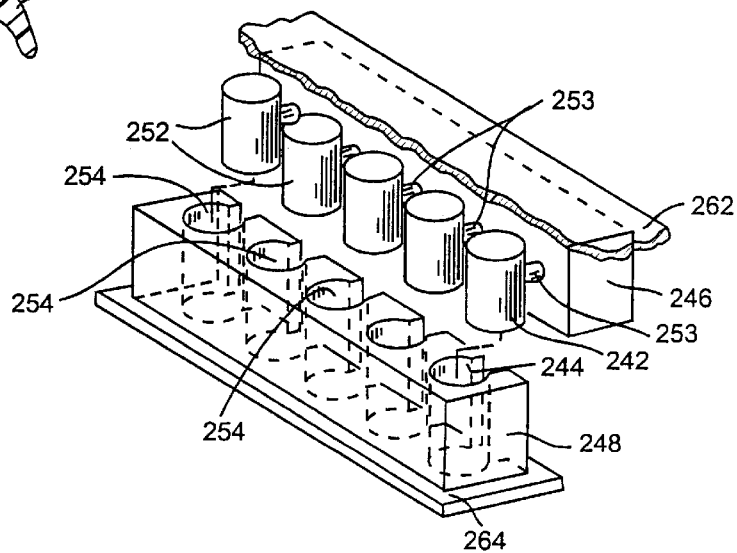
FIG. 26 is an expanded perspective view of the adjustment mechanism shown in FIG. 23.
Figure 27:
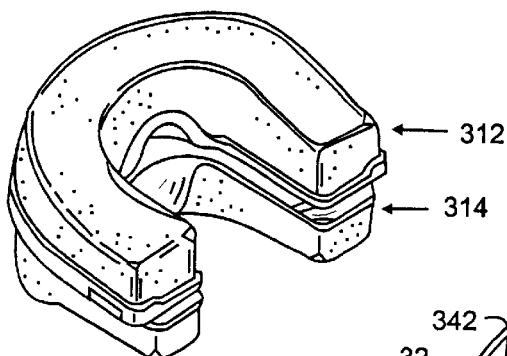
FIG. 27 is a perspective view of another embodiment of the invention which comprises upper and lower members.
Figure 29:
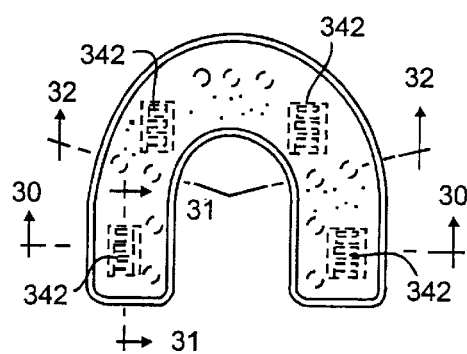
FIG. 29 is a top plan view of an upper member of the apparatus shown in FIG. 28.
Figure 28:
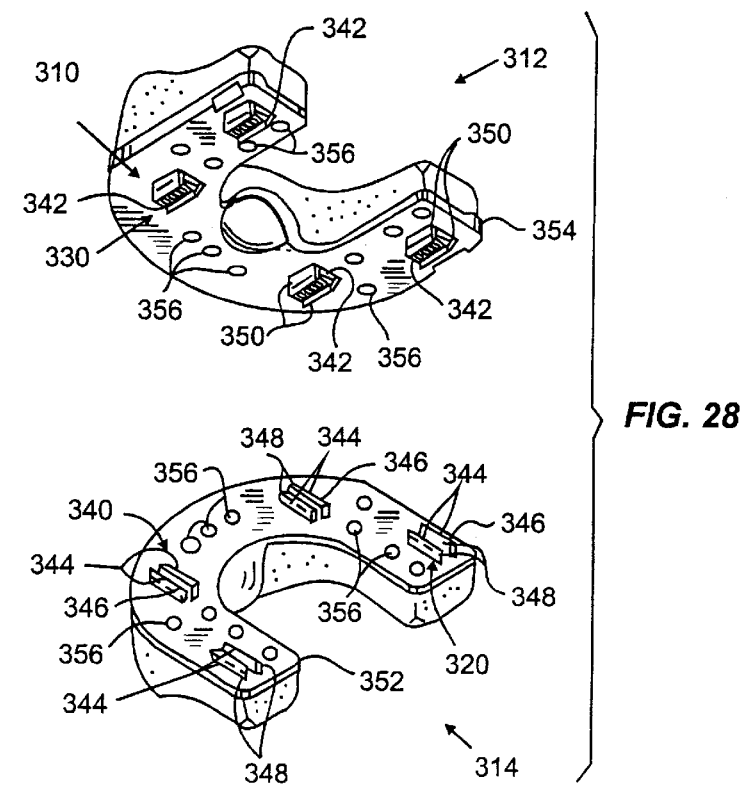
FIG. 28 is an exploded perspective view of the apparatus shown in FIG. 27.

As shown most clearly in FIG. 18, the longitudinal screw 160 is received in the block 156 extending from the upper plate 152 through a socket 157 formed within the block 156. The socket 157 has a hole 159 therein which is large enough to allow the longitudinal screw 160 to pass freely through the hole. The hole is sufficiently small, however, to retain the head 162 of the longitudinal screw 160 within the socket 157. In this way, the head 162 of the longitudinal screw is free to rotate within the socket 157, but the longitudinal screw 160 cannot move forward or backward with respect to the block 156.

Figure 17:
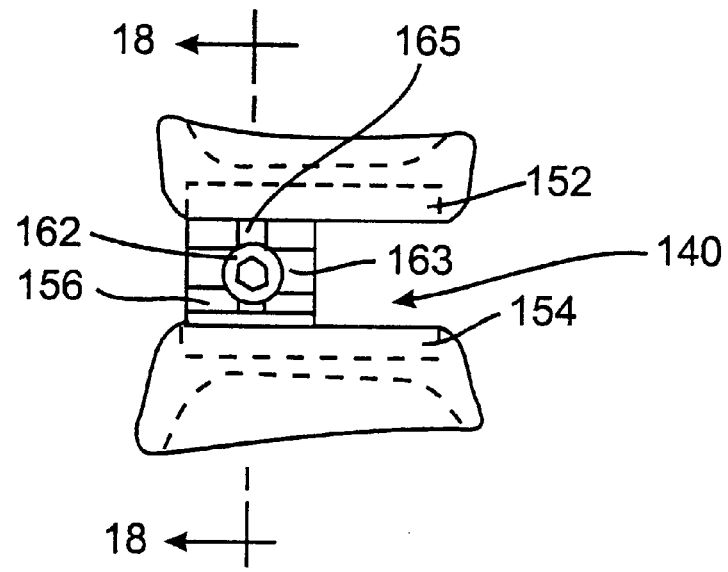
FIG. 17 is a rear view of the right side of the apparatus shown in FIG. 7.

The block 156 preferably has a cylindrical bore 161 therein which intersects with the socket 157. In FIG. 18, the cylindrical bore 161 has an axis which projects out of the page. The radius of the cylindrical bore 161 is preferably made sufficiently large to allow the head 162 of the longitudinal screw 160 to be inserted through the cylindrical bore 161 into the socket 157 during assembly of the device. As shown in FIG. 17, the block 156 may also be provided with a horizontal channel 163 and a vertical channel 165 which intersect the socket. The horizontal channel 163 and the vertical channel 165 allow the longitudinal screw 160 to be rotated about different axes after the head 162 is inserted into the socket so that the head 162 faces the rear of the apparatus. Thus, the head 162 may be inserted through the cylindrical bore 161 into the socket 157, rotated about one axis through the horizontal channel 163, and rotated about a perpendicular axis through the vertical channel 165 so that the head can be oriented to face rearward.

The longitudinal screw 160 is screwed into a threaded hole 167 of the other block 158 extending from the lower plate 154. The rotation of the screw 160 adjusts the longitudinal position of the screw with respect to the block 158. Thus, by turning the screw 160, the relative longitudinal positions of the upper and lower members 120 and 130 can be adjusted. That is, the longitudinal screw 160 allows adjustment of the upper and lower members 120 and 130 relative to one another front to back and back to front in relation to the user's mouth. The longitudinal screw 160 also serves to attach the upper member 120 to the lower member 130. As best shown in FIG. 17, the head 162 of the longitudinal screw 160 preferably faces the rear end of the apparatus so as to facilitate adjustment of the apparatus, for example with a small screwdriver or allen wrench.

The blocks 156 and 158 preferably project from the upper and lower members 120 and 130 on the inside of the members and do not occupy the entire width of the members, as shown in FIG. 17, so that a breathing channel 140 is formed between the members adjacent to the outside edge of the blocks 156 and 158. The breathing channel allows air to pass from the throat out the front of the mouth along the sides of the apparatus.

The forward and backward positioning of the upper member 120 with respect to the lower member 130 can be adjusted by adjusting the longitudinal screw 160 in the upper and lower blocks 156 and 158. The adjustment device 150 thus allows for precise adjustment of the relative positions of the upper and lower members at any time during the patient's use of the device. For example, when the patient is first fitted for the device, the adjustment device can be used to achieve the exact desired positioning of the maxillary teeth relative to the mandibular teeth. In addition, as the patient becomes accustomed to the device, it may be desirable to make further adjustments in the relative positioning of the upper and lower members 120 and 130, for example, to improve the effectiveness of the device or to reduce any discomfort experienced by the user. The adjustment device thus allows the doctor and patient to precisely obtain the desired position of the mandible, for example for comfort and elimination of snoring and related problems, without the need to refit or fabricate a new apparatus.

FIGS. 12–16 show an embodiment of the invention in which an adjustment device 175 comprises longitudinal screws 170 for adjusting the relative forward and backward positions of the upper and lower members 180 and 190 as well as vertical screws 172 for adjusting a separation distance between the upper and lower members 180 and 190. According to this embodiment, at least one and preferably two vertical screws 172 are provided on each side (left and right) of the apparatus to adjust the separation distance between the upper and lower members 180 and 190. The vertical screws 172 at one end thereof may be received into screw holes in the upper member 180 or lower member 190. The other end of the vertical screw 172, which may be rounded, makes contact with the other member to establish a separation distance between the upper and lower members.

Figure 14:
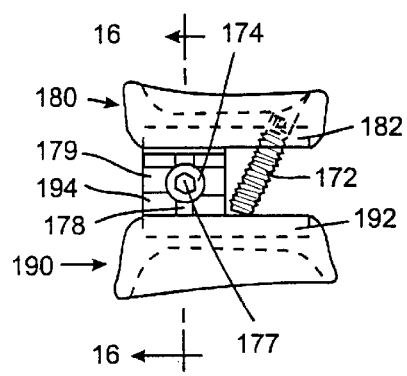
FIG. 14 is a rear view of the right side of the apparatus shown in FIG. 12.
Figure 15:
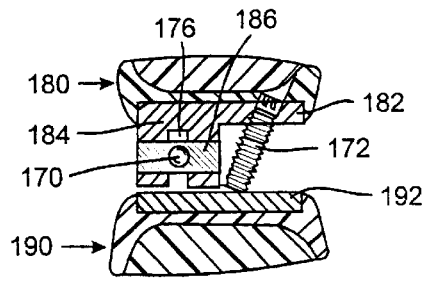
FIG. 15 is a rear cross-sectional view of the right side of the apparatus shown in FIG. 12.

As shown in FIGS. 14 and 15, the vertical screws 172 are preferably angled in such a way that the holes in the plate 182 which receive the vertical screws 172 are located toward the outer edge of the plate 182. Thus, as shown in FIGS. 14 and 15, by angling the vertical screws 172 toward the outer edge of the plate 182, the bottom of the screws 172 can contact the lower plate 192 proximate to the center of the plate 192, while the threaded holes in the upper plate 182 can be placed toward the outer edge of the plate 182. The angle of the vertical screws 172 is preferably about 20 degrees from vertical. The location of the holes toward the outer edge of the plate minimizes the interference of the holes with the maxillary teeth.

Figure 12:
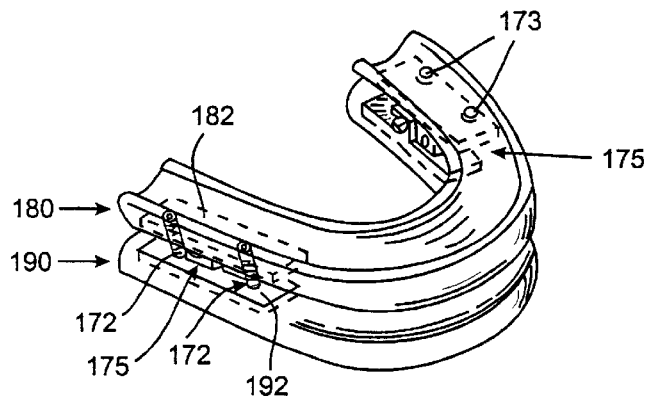
FIG. 12 is a perspective view of another embodiment of the invention which comprises upper and lower members.
Figure 13:
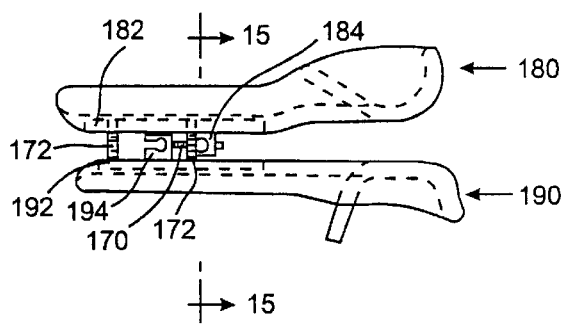
FIG. 13 is a side view of the apparatus shown in FIG. 12.

As shown in FIG. 12, the vertical screws 172 can have a recess 173, such as a hexagonal recess to receive an allen wrench or any other recess to receive an adjustment tool such as a screwdriver, formed at one end thereof within the outer diameter of the vertical screw 172. By turning each vertical screw 172 with an allen wrench or other suitable tool, the separation distance between the upper and lower members may be adjusted.

The upper and lower members 180 and 190 in the embodiment shown in FIGS. 12–16 can be constructed in the same manner as described above with respect to the upper and lower members 120 and 130 shown in FIGS. 7–10. For brevity, the discussion of the construction and features of the upper and lower members will not be repeated. However, it will be readily apparent to one skilled in the art that the same features described with respect to members 120 and 130, such as the resin layer, the perpendicularly extending flange, the breathing channel, etc., can be included in the members 180 and 190.

Figure 16:
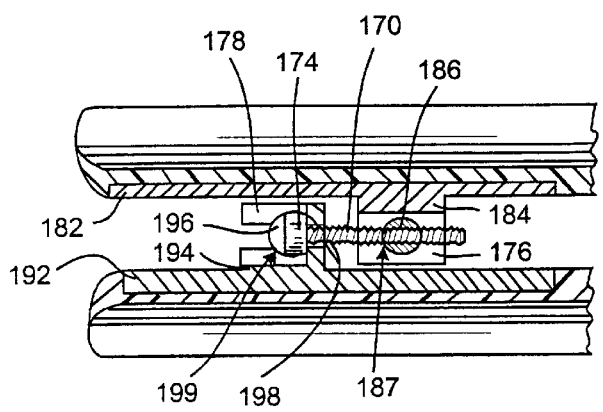
FIG. 16 is a side cross-sectional view of an exemplary adjustment mechanism shown in FIG. 12.

The embodiment shown in FIGS. 12–16 includes upper and lower plates 182 and 192 which are embedded in the resilient semi-rigid material of the upper and lower members 180 and 190 at the rear molar area of the apparatus. Projecting from the upper and lower plates 182 and 192 are blocks 184 and 194, respectively, which receive the longitudinal screws 170. The blocks 184 and 194 are provided with a means for receiving the longitudinal screw 170 at different angles. As shown in FIG. 16, the upper block 184 includes a cylinder 186 disposed within a cylindrical opening in the block 184 such that the cylinder 186 can rotate within the cylindrical opening. The cylinder 186 includes a threaded hole 187 for receiving the longitudinal screw 170. The longitudinal screw 170 may thus be received into the upper block 184 from a range of angles due to the ability of the cylinder 186 to rotate within the cylindrical hole of the block 184.

The lower block 194 shown in FIG. 16 includes a socket 196 having a hole 198 therein through which the longitudinal screw 170 is received. The hole 198 has a size which is sufficiently large that the longitudinal screw 170 is free to project outwardly from the block 194 at different angles. The hole 198 is sufficiently small, however, that a head 174 of the longitudinal screw 170 prevents the end of the screw 170 from leaving the socket 196. As shown in FIG. 14, the head 174 of the longitudinal screw 170 may comprise a hexagonal opening 177 or any other appropriate shape to receive an allen wrench or any other suitable tool such as a screwdriver for rotating the screw.

As is seen most clearly in FIGS. 14–16, both the upper block 184 and the lower block 194 may have a channel cut therethrough to allow the longitudinal screw 170 to pass through the block at different angles. Thus, an upper vertical channel 176 may be formed in the upper block 184 and a lower vertical channel 178 may be formed in the lower block 194. FIG. 16 shows a cross section of the apparatus cut through the channels 176 and 178.

The upper and lower vertical channels 176 and 178 allow the longitudinal screw 170 to be received in both the upper and the lower blocks 184 and 194 from a range of angles. This feature allows for simultaneous adjustment of the relative forward and backward positions of the upper and lower members 180 and 190 with the longitudinal screw 170 as well as adjustment of the separation distance between the upper and lower members 180 and 190 with the vertical screws 172. Thus, the adjustment device of FIGS. 12–16 provides great flexibility in adjusting the relative positioning of the upper and lower members 180 and 190, which may be advantageously utilized by the doctor to precisely align the upper and lower members at any time during treatment without the need to refit or refabricate the apparatus.

As described above with respect to the embodiment shown in FIGS. 7–10 and 17–18, the block containing the socket may advantageously include a cylindrical bore 199 intersecting the socket 196 as well as horizontal and vertical channels. The horizontal and vertical channels 179 and 178, respectively, shown in FIG. 14, along with the cylindrical bore intersecting the socket 196, allow the head of the screw to be inserted into the socket through the cylindrical bore and rotated into proper alignment to face the rear of the apparatus. Thus, during assembly of the device, the head 174 of the longitudinal screw 170 may be inserted through the cylindrical bore 199 into the socket 196. The longitudinal screw 170 may then be rotated about one axis through the horizontal channel 179 and about a perpendicular axis through the vertical channel 178 such that the head 174 of the longitudinal screw 170 faces the rear of the apparatus.

FIGS. 19 through 22 show an embodiment of the invention in which an adjustment device 220 comprises reciprocal surfaces 222 and 224 for adjusting the relative forward and backward positions of the upper and lower members 230 and 240. As shown most clearly in FIG. 22, the reciprocal surfaces 222 and 224 may be formed in a saw tooth pattern. Each member, upper and lower, thus includes a block 226, 228 having a saw tooth pattern. For clarity, the saw tooth pattern shown in FIGS. 19–22 has a relatively small number of teeth. However, the teeth can be made to be any desired size, for example to allow for more precise adjustment with smaller teeth.

The blocks 226 and 228 may be fixed to the plates 232 and 234 which are embedded in the upper and lower members 230 and 240. Alternatively, the upper member 230 may be formed integrally with the upper block 226 from a single mold. The lower member 240 may be formed integrally with the lower block 228 from a single mold. Forming the upper member and upper block from a single mold and the lower member and lower block from a single mold reduces the manufacturing cost appreciably.

As shown in FIG. 21, the reciprocal surfaces 222 and 224 of the upper and lower blocks 226 and 228 fit together to fix the relative forward and backward positions of the upper and lower members 230 and 240. The adjustment device 220 thus allows a user to easily adjust the relative forward and backward positions of the upper member 230 with respect to the lower member 240 in a discreet number of positions. Also shown in FIG. 21 is a screw 236 which can be used to secure the two blocks 226 and 228 together after they have been adjusted to the desired position. A threaded hole can be formed in one of the blocks whenever the relative positions of the upper and lower members are adjusted.

For brevity, a description of the upper and lower members will be omitted. However, it will be readily appreciated by those skilled in the art that the upper and lower members can be constructed to have all of the features described in previous embodiments, such as the resin layer, the perpendicularly extending flange, the front and rear walls, the breathing channel, etc.

FIGS. 23 through 26 show an embodiment of the invention in which the interlocking surfaces 242 and 244 of the upper and lower blocks 246 and 248 comprise a series of cylindrical projections 252 which interlock with a reciprocal series of cylindrical openings 254. The cylinders 252 can be placed inside the cylindrical openings 254 to fix the relative forward and backward position of the upper member 250 with respect to the lower member 260. The cylinders 252 may be attached to the block 246 with projections 253 of any suitable form. The adjustment device according to this embodiment thus allows easy adjustment to a number of discreet adjustment positions as with the embodiment shown in FIGS. 19–22. For clarity, the number of cylinders shown in FIGS. 23–26 is relatively small. However, a greater number of smaller cylinders can be implemented, for example if more precise adjustment is desired. The cylinders 252 which fit snugly within the cylindrical openings 254 provide a secure, interlocking attachment of the upper member 250 to the lower member 260, which dispenses with the need for a securing screw. However, as in the embodiment shown in FIGS. 19–22, a securing screw (not shown in FIGS. 23–26) can be used to lock the upper block 246 to the lower block 248. The screw may thus pass through the lower block 248 having the cylindrical openings and into one of the cylinders 252.

The upper block 246 and the lower block 248 can be attached to plate 262 and 264 which are embedded in the upper and lower members 250 and 260, respectively. Alternatively, the upper and lower blocks 246 and 248 can be formed integrally with the upper and lower members 250 and 260, respectively, out of a single mold. Forming the upper member and upper block from a single mold and the lower member and lower block from a single mold reduces the manufacturing cost appreciably.

For brevity, a description of the upper and lower members will be omitted. However, it will be apparent that the upper and lower members can be constructed to have all of the features described in previous embodiments, such as the resin layer, the perpendicularly extending flange, the front and rear walls, the breathing channel, etc.

Figure 30:
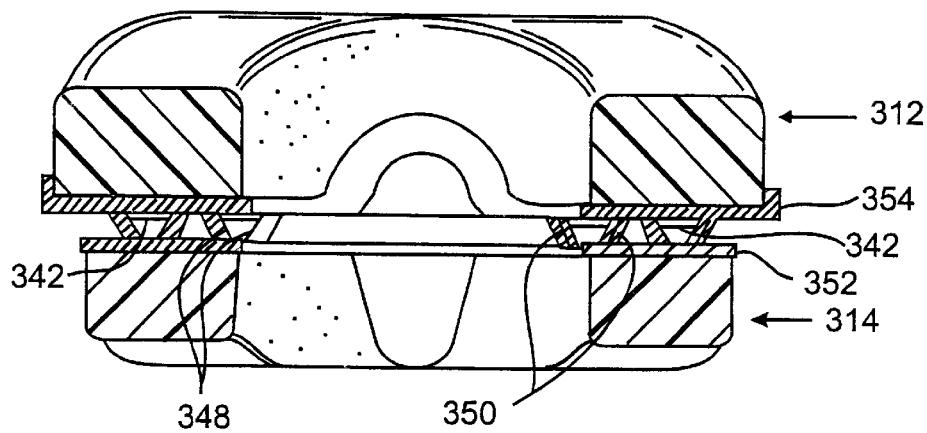
FIG. 30 is a cross-sectional view along line 30—30 of the apparatus shown in FIG. 29.
Figure 31:
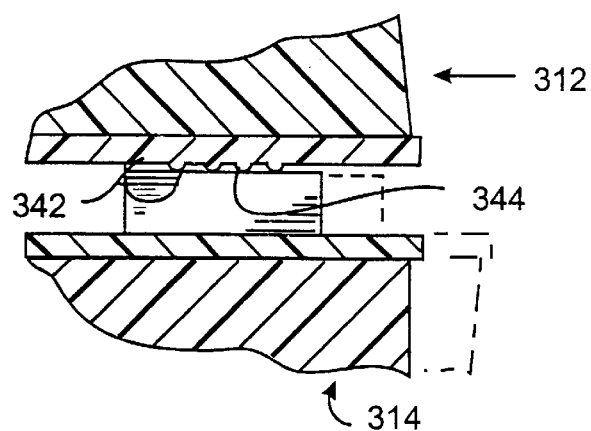
FIG. 31 is a cross-sectional view along line 31—31 of the apparatus shown in FIG. 29.
Figure 32:
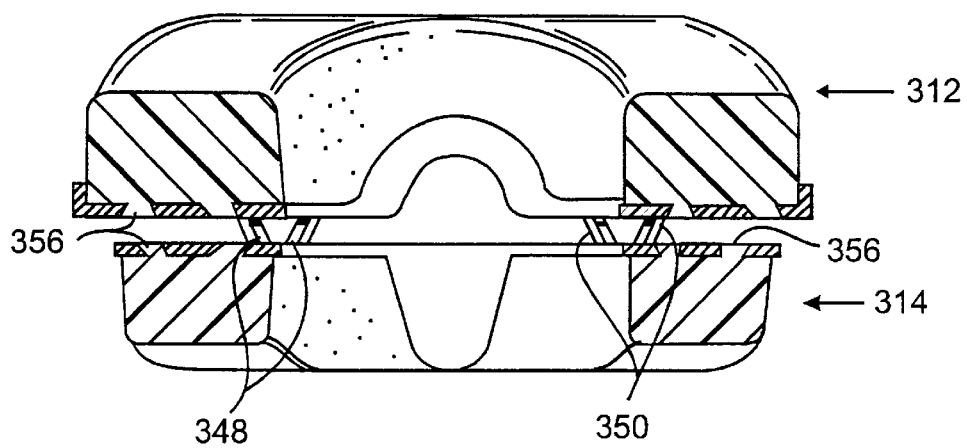
FIG. 32 is a cross-sectional view along line 32—32 of the apparatus shown in FIG. 29.

FIGS. 27 through 32 show an embodiment of the invention in which the interlocking surfaces 330 and 340 of the upper block 310 and the lower block 320, respectively, comprise a series of projections 342 which interlock with a reciprocal series of raised detents or bumps 344. The raised detents or bumps 344 can be positioned between the projections 342 to fix the relative forward and backward position of the upper member 312 with respect to the lower member 314. The raised detents or bumps 344 are located on outer surfaces 346 of first dovetail members 348, which extend from plate 352 of lower member 314. As more easily seen in FIGS. 30 and 32, first dovetail members 348 extend from plate 352 at a first angle thereto. The projections 342 are located on or adjacent to plate 354 of upper member 312, and between second dovetail members 350. As more easily seen in FIGS. 30 and 32, second dovetail members 350 extend from plate 354 at a second angle thereto. The separation distances between the first dovetail members 348 and the second dovetail members 350, and the first and second angles, are selected such that first dovetail members 348 dovetail with second dovetail members 350, as illustrated in FIGS. 30 and 32, to provide mutual lateral support to upper member 312 and lower member 314, and to prevent their mutual lateral displacement.

The adjustment device according to this embodiment thus allows easy adjustment to a number of discreet adjustment positions as with the embodiments shown in FIGS. 19–22 and 23–26. FIG. 31 illustrates, in phantom lines, one position to which lower member 314 can be moved and securely positioned relative to upper member 312. For clarity, the number of projections 342 shown in FIGS. 27–32 is relatively small. However, a greater number of smaller projections can be implemented, with a correspondingly smaller raised detent or bump, for example if more precise adjustment is desired. The raised detents or bumps 344 which fit snugly within the spaces between projections 342 provide a secure, interlocking attachment of the upper block 310 to the lower block 320, which dispenses with the need for a securing screw. However, as in the embodiments shown in FIGS. 19–22 and 23–26, a securing screw (not shown in FIGS. 23–26) can be used to lock the upper block 310 to the lower block 320. The screw may thus pass through the lower block 320 between the raised detents or bumps and into the projections 342.

The upper block 310 and the lower block 320 can be attached to plates 352 and 354, which are embedded in the upper and lower members 312 and 314, respectively, via embedding bores 356. Alternatively, the upper and lower blocks 310 and 320 can be formed integrally with the upper and lower members 312 and 314, respectively, out of a single mold. Forming the upper member 312 and upper block 310 from a single mold and the lower member 314 and lower block 320 from a single mold reduces the manufacturing cost appreciably.

Upper member 312 and lower member 314 optionally can be fixed together after their relative positions have been adjusted. With the raised detents or bumps 344 positioned between and interlocking with projections 342, plate 352 can be permanently joined to plate 354, upper block 310 can be permanently joined to lower block 320, or both. Permanently joining plates 352 and 354, and/or upper and lower blocks 310 and 320, eliminates the possibility of upper member 312 moving relative to lower member 314, thus ensuring that the oral apparatus of the present invention always correctly fits the jaws of the wearer. Plates 352 and 354, and upper and lower blocks 310 and 320, can be permanently joined by glue, ultrasonic welding, heat welding, or other means as will be readily apparent to one of ordinary skill in the art.

For brevity, a description of the upper and lower members will be omitted. However, it will be apparent that the upper and lower members can be constructed to have all of the features described in previous embodiments, such as the resin layer, the perpendicularly extending flange, the front and rear walls, the breathing channel, etc.

The foregoing description of the specific embodiments will so fully reveal the general nature of the invention that others can, by applying current knowledge, readily adapt for various applications such specific embodiments without departing from the generic concept, and, therefore, such adaptations and modifications should and are intended to be comprehended within the meaning and range of equivalents of the disclosed embodiments. For example, those skilled in the art will readily appreciate that many other configurations and variations of the adjustment device can be utilized in conjunction with the present invention. It is to be understood that the phraseology of terminology employed herein is for the purpose of description and not of limitation.

What is claimed is:

1. An apparatus for intra-oral use comprising:
    upper means for snugly fitting over maxillary teeth of a user:
    lower means, connected to the upper means, for loosely fitting over mandibular teeth of the user so as to allow the mandibular teeth to approach the maxillary teeth and come to rest in a normal closing arch such that a relative position of the maxillary teeth and the mandibular teeth when the apparatus is worn is the same as when the apparatus is not worn and to allow freedom of movement of the mandible in forward and side to side directions while preventing rear movement of the mandible; and
    adjustment means, connected to the upper and lower means, for adjusting a position of the upper means with respect to a position of the lower means;
    wherein the adjustment means comprises:
        a substantially horizontal longitudinal screw which controls a forward and backward adjustment of the upper means with respect to the lower means; and
        at least one vertical screw which controls a separation distance between a bottom surface of the upper means and a top surface of the lower means.

2. The apparatus of claim 1, wherein the adjustment means further comprises:
    a first block into which the longitudinal screw is received, the first block fixed to the upper means; and
    a second block into which the longitudinal screw is received, the second block fixed to the lower means, wherein at least one of the first block and the second block is adapted to receive the longitudinal screw at more than one angle.

3. The apparatus of claim 2, wherein at least one of the first block and the second block includes a cylinder which receives the longitudinal screw and which rotates within the block to receive the longitudinal screw at different angles.

4. The apparatus of claim 2, wherein at least one of the first block and the second block includes a socket which receives a head of the longitudinal screw and which allows the longitudinal screw to project from the block at different angles.

5. The apparatus for intra-oral use according to claim 1, wherein said substantially horizontal longitudinal screw adjusts a forward and backward position of the upper member with respect to the lower member independent of said separation distance controlled by said at least one vertical screw.

6. An apparatus for intra-oral use comprising:
    upper means for snugly fitting over maxillary teeth of a user;
    lower means for loosely abutting mandibular teeth of the user so as to allow the mandibular teeth to approach the maxillary teeth and come to rest in a normal closing arch such that a relative position of the maxillary teeth and the mandibular teeth when the apparatus is worn is the same as when the apparatus is not worn, the lower means comprising a substantially flat surface to allow freedom of movement of the mandible in forward and side to side directions, and a stop which prevents rear movement of the mandible; and
    adjustable connecting means, connected to the upper and lower means, for connecting the upper means and lower means and for adjusting a position of the upper means with respect to a position of the lower means when the upper and lower means are connected;
    wherein the adjustable connecting means comprises a first block extending from the upper means, and a second block extending from the lower means, wherein the first block and the second block have reciprocal surfaces which fix a forward and backward position of the upper means with respect to the lower means;
    wherein said first block further comprises a first pair of dovetail members, and said second block further comprises a second pair of dovetail members for being received in said first pair of dovetail members, said first and second dovetail members together supporting said upper and lower means against lateral displacement when said upper and lower means are connected by said adjustable connecting means.

* * * * *